United States Patent
Hemmendorff et al.

(10) Patent No.: US 7,232,894 B1
(45) Date of Patent: Jun. 19, 2007

(54) METHOD FOR THE PRODUCTION OF RECOMBINANT PEPTIDES WITH A LOW AMOUNT OF TRISULFIDES

(75) Inventors: Barbro Hemmendorff, Huddinge (SE); Andreas Castan, Hägersten (SE); Anders Persson, Uppsala (SE)

(73) Assignee: Pharmacia AB, Stockholm (SE)

( * ) Notice: Subject to any disclaimer, the term of this patent is extended or adjusted under 35 U.S.C. 154(b) by 612 days.

(21) Appl. No.: 09/743,023

(22) PCT Filed: Jul. 5, 1999

(86) PCT No.: PCT/SE99/01222

§ 371 (c)(1),
(2), (4) Date: Mar. 7, 2001

(87) PCT Pub. No.: WO00/02900

PCT Pub. Date: Jan. 20, 2000

(30) Foreign Application Priority Data

Jul. 8, 1998 (SE) .................................... 9802454

(51) Int. Cl.
*C07K 1/14* (2006.01)
*C07K 1/113* (2006.01)
*C07K 14/61* (2006.01)
*A61K 38/27* (2006.01)

(52) U.S. Cl. ...................... 530/418; 530/399; 530/412; 530/419; 530/420

(58) Field of Classification Search ................ 530/350, 530/351; 436/15; 435/320.1
See application file for complete search history.

(56) References Cited

U.S. PATENT DOCUMENTS 4,985,544 A * 1/1991 Yokoo et al. ................ 530/399
5,256,546 A * 10/1993 Aviv et al. .................. 435/69.4
5,663,304 A * 9/1997 Builder et al. .............. 530/399

FOREIGN PATENT DOCUMENTS

| WO | WO 9424157 | 10/1994 |
|---|---|---|
| WO | WO-9424157 A1 * | 10/1994 |
| WO | WO 9506064 | 3/1995 |
| WO | WO 9602570 | 2/1996 |
| WO | WO-9602570 A1 * | 2/1996 |

OTHER PUBLICATIONS

Breton et al. ("Detection of traces of a trisulphide derivative in the preparation of a recombinant truncated interlukin-6 mutein", J. Chromatography, vol. 709, 1995, 135-146.*
Pavlu, et al, Hydrophobic Interaction Chromatography of Recombinant Human Growth Hormone, Genotropin®, *Bioseparation*, vol. 3, pp. 257-265 (1993).
Andersson, et al, Isolation and Characterization of a Trisulfide Variant of Recombinant Human Growth Hormone Formed During Expression in *Escherichia coli, Int. J. Peptide Protein Res.*, vol. 47, pp. 311-321 (1996).
Briggs, et al, Sulfhydryl Reactivity of Human Erythrocyte Superoxide Dismutase On The Origin Of The Unusual Spectral Properties of the Protein When Prepared by a Procedure Utilizing Chloroform and Ethanol for the Precipitation of Hemoglobin, *Biochimica et Biophysica Acta*, vol. 537, pp. 100-109 (1978).
Breton[a] et al, Detection of Traces of a Trisulphide Derivative in the Preparation of a Recombinant Truncated Interleukin-6 Mutein, *Journal of Chromatography A*, vol. 709, pp. 135-146 (1995).

* cited by examiner

*Primary Examiner*—Christine J. Saoud
(74) *Attorney, Agent, or Firm*—Dinsmore & Shohl LLP

(57) ABSTRACT

Methods for the production of recombinant peptides comprise fermenting cells to produce recombinant peptides. A metal salt is added to a concentrate of the fermented cells after the fermentation step, prior to peptide isolation, and the pH of the cell concentrate after the addition of the metal salt is less than or equal to 7, thereby reducing the amount of trifulsides formed in the production of the recombinant peptide, with the proviso that the production does not include conversion of formed trifulside peptide into native peptide form after the addition of the metal salt. In one embodiment, the recombinant peptide is recombinant growth hormone.

13 Claims, 2 Drawing Sheets

METHOD FOR THE PRODUCTION OF RECOMBINANT PEPTIDES WITH A LOW AMOUNT OF TRISULFIDES

The invention relates to a method for the production of recombinant peptides with a low amount of trifulsides which is characterized by the addition of a metal salt during or after the fermentation step and to a method for reduction of the amount of trifulsides in the production of recombinant peptides, characterized by the addition of a metal salt during or after fermentation. The peptide is preferably human growth hormone and the salt preferably a potassium or sodium phosphate.

BACKGROUND OF THE INVENTION

In the recombinant production of peptides, especially in the production of pharmaceuticals, the amount of contamination, such as variants of the wanted protein, should be reduced as much as possible both from economical and therapeutical aspects.

In the recombinant production of peptides, variants with an extra sulfur atom in a disulfide bridge sometimes are found, and the present invention relates to this problem.

Human Growth hormone, hGH, is a protein consisting of a single chain of 191 amino acids. The molecule is cross-linked by two disulfide bridges and the monomeric form has a molecular weight of 22 kDa.

hGH preparations have been prepared from human pituitaries, but nowadays the products on the market are produced by recombinant methods, rhGH.

Two types of therapeutically useful recombinant hGH preparations are present on the market: the authentic one, e.g. Genotropin®, Pharmacia & Upjohn AB, and an analogue with an additional methionine residue at the N-terminal end, e.g. Somatonorm®.

hGH is used to stimulate linear growth in patients with hypo pituitary dwarfism or Turner's syndrome but other indications have also been suggested.

A new variant of human growth hormone, hGH, has been found and reference is given to Pavlu et al, 1993, Bioseparation 3, 257-265. This variant has been identified and characterized, see Andersson et al, 1996, Int. J. Peptide, Protein,. Res. 47, 311-321. The variant, which is formed during the expression of hGH in Escherichia coli, is found to be more hydrophobic than rhGH and has been structurally defined as a trisulfide variant of rhGH.

The variant is only formed during synthesis in *E Coli* and has not been found in hGH preparations from human pituitaries.

This phenomenon of the trifulsides in peptides, produced by recombinant methods, has also been described for recombinant superoxide dismutase (Briggs et al, 1987, Biochem. Biophys. Acta, 537, 100-109) and for a mutein of interleukin, (Breton J et al. J. Chromatogr. A., 1995, 709(1), 135-46).

In WO 94/24127 a method for converting a hydrophobic derivative of a growth hormone into the native form of growth hormone is disclosed. The hydrophobic derivative of the growth hormone comprises an extra sulfur atom. The method is a chemical treatment of the derivative of growth hormone with a mercapto compound. As examples are cystein, gluthatione, 2-mercapto ethanol and dithiothreitol given.

In WO 96/02570 a method is disclosed comprising the chemical treatment with a sulfite compound for the conversion of the derivative of growth hormone into the native form. Mercapto compounds and sulfite compounds are used in the redox-reaction for the conversion of the already formed growth hormone comprising an extra sulfur atom.

SUMMARY OF THE INVENTION

We have now found a new method for the reduction of the amount of trifulsides in the production of recombinant peptides, e.g. both proteins and smaller peptides.

The invention is based on the novel and unexpected finding that the amount of trisulfides in the production of recombinant peptides can be reduced by the addition of a metal salt, preferably in excess, already during or after fermentation and not, as earlier suggested, by conversion of the formed trisulfide of growth hormone into the native form.

This reduced amount of the derivative is due to inhibition of the activity of $H_2S$ in the medium and the prevention of the formation of the modified growth hormone comprising an extra sulfur atom.

The addition can be done directly after fermentation, e.g. after the fermentation has been terminated and the cells are harvested and before further process steps.

The addition can e.g. be done with a buffer including the salt.

The protein can be any recombinant protein but is preferably recombinant growth hormone which can be both human and animal such as human growth hormone (hGH), bovine growth hormone (bGH) and porcine growth hormone (pGH).

The metal salt can be any metal chosen among alkalimetal and earth metal.

pH is preferably equal to or lower than pH 7. More preferable pH is equal to or lower than 6.8 and most preferable pH is equal to or lower than 6.0.

The pH regulation can be achieved with a selected buffer including the metal salt.

The metal is preferably alkali, such as sodium or potassium and the salt is preferably sodium or potassium phosphate or acetate.

The concentration of free sulfide ions is minimized by addition of the metal salt in molar excess.

The used metal salt is preferably not a sulfite or a mercapto compound.

The attached claims define the invention.

BRIEF DESCRIPTION OF THE DRAWING

The invention is further illustrated and better understood in view of the drawings in which.

In the examples below a recombinant produced hGH has been produced or used, but the invention as claimed is not limited to this peptide. The trisulfide variant is named trisulfide-GH.

EXAMPLES hGH was produced in *E. Coli* according to known methods. Reference can be given to EP 177343, example 8.

The transformant of *E. Coli* was fermented in the medium, the culture was agitated under aeration and glucose was added. The fermentation was terminated by turning off the glucose and aeration. At this point a reference sample was taken. Thereafter the cells were harvested.

For the production of pure hGH, the harvested cells were concentrated, washed, solubilized by freezing, thawed and purified according to known methods.

Example 1 pH Variation, Lab Scale

The culture was harvested and the cells were concentrated by microfiltration. The pH was 7.3 in the cell concentrate. Four batches of the cell concentrate were taken. In three batches (500 ml) the pH was adjusted to 6.5, 7.0 and 7.8, with HCl or NaOH, respectively. The fourth batch is the non-treated comparison sample. Thereafter the cell concentrates were frozen.

The four batches were thawed and the cell concentrates were diluted twice with a buffer containing 10 mM Tris-HCl and 1 mM $Na_2$-EDTA pH 8.2. Cell free extracts were obtained by centrifugation.

The amount of trisulfide-GH in the extracts was determined.

Figure 1:
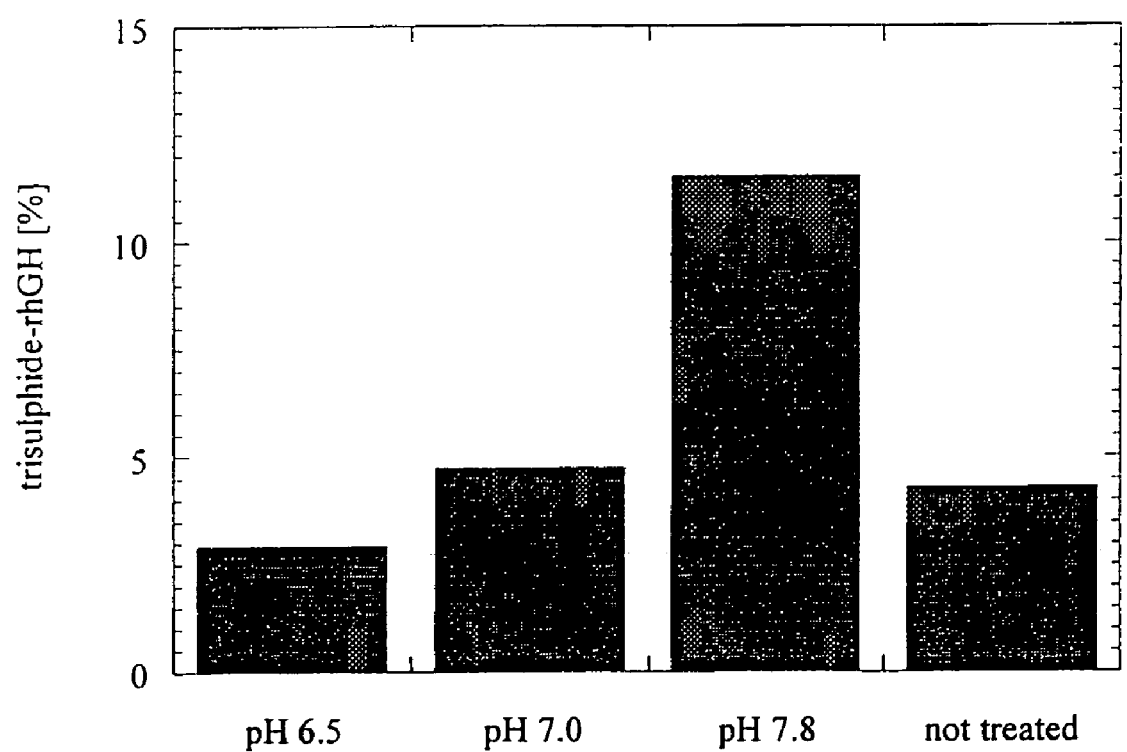
FIG. 1 shows the amount of trisulfide-GH in the extracts.

The result is shown in FIG. 1.

It was found that the amount of trisulfide-GH was highest at pH 7.8 (12%). This could be compared to the fourth batch which was not pH-changed.

A pH above 7.0 gave too high amount of trisulfide-GH in this experiment, thus pH should be lower.

Example 2

Pilot Scale

The culture was harvested and the cells were concentrated by microfiltration. The pH in the cell concentrate was 7.2. The cell concentrate was divided in two portions (about 30 L).

Cell concentrate A was washed with about one volume of water and was thereafter frozen at −30° C.

Cell concentrate B was washed with about one volume of 0.05 M potassium phosphate buffer, pH 6.6. The pH in cell concentrate B was 6.8. The cell concentrate was thereafter frozen at −30° C.

After thawing, the concentrated cells were extracted by diafiltration with Tris-HCl/EDTA buffer and the amount of trisulfides was determined. The amount of trisulfide-GH was 6% in extract A and about 3% in extract B, thus the double in A compared to B. This showed that low pH and the metal salt buffer reduces the amount of the trisulfide variant of growth hormone.

Example 3

Pilot Scale

The amount of trifulsides in the reference sample, taken before harvest, was determined.

The culture was harvested and the cells were concentrated by microfiltration. The pH in the cell concentrate was 7.2. The cell concentrate was divided in two portions (about 30 L).

Cell concentrate C was washed with about one volume of water and was thereafter frozen at −30° C.

Cell concentrate D was washed with about one volume of 0.9% NaCl in water. The pH in that cell concentrate was 7.2. The cell concentrate was thereafter frozen at −30° C.

After thawing, the concentrated cells were extracted by diafiltration with Tris-HCl/EDTA buffer and the amount of trisulfides was determined. The amount of trisulfide-GH was about 5% in extract C and about 4.8% in D, thus the same in C and D. The ratio of trisulfide-GH in extract C: reference sample was 5.0%:2.0%=2.5 and the ratio of trisulfide-GH in extract D: reference sample was 4.7%:2.0%=2.4

This showed that for a periplasmatic extract not only the addition of a metal salt but also the low pH is of importance.

Example 4

Pilot Scale

The amount of trisulfides in the reference sample, taken before harvest, was determined.

The culture was harvested and the cells were concentrated by microfiltration. The pH in the cell concentrate was 7.2. The cell concentrate (E) was washed with about one volume of 0.025 M sodium phosphate buffer pH 6.0, to which 1 ml/L HCl 37% was added. The pH in cell concentrate E was 5.9. The cell concentrate was thereafter frozen at −30° C.

After thawing the concentrated cells were extracted by diafiltration with Tris-HCl/EDTA buffer and the amount of trisulfides was determined.

The ratio of trisulfide-GH in extract E: reference sample was 1.6%:1.4%=1.1.

This showed that the amount of trisulfide-GH can be reduced by the addition of a metal salt and a low pH.

Example 5

Pilot Scale

The amount of trisulfides in the reference sample, taken before harvest, was determined.

The culture was harvested and the cells were concentrated by microfiltration. The pH in the cell concentrate was 7.2. The cell concentrate was divided in two portions (about 30 L).

Cell concentrate F was washed with about one volume of acetate buffer, containing sodium acetate×$3H_2O$, 8.03 g/L and acetic acid (100%) 2.35 ml/L. The pH in cell concentrate F was 5.9. The cell concentrate was thereafter frozen at −30° C.

Cell concentrate G was washed with about one volume of 0.025 M sodium phosphate buffer pH 6.0, to which 0.5 ml/L concentrated $H_2SO_4$ was added. The pH in cell concentrate G was 5.9. The cell concentrate was thereafter frozen at −30° C.

After thawing the concentrated cells were extracted by diafiltration with Tris-HCl/EDTA buffer and the amount of trisulfides was determined.

The ratio of trisulfide-GH in extract F: reference sample was 3.4%:3.1%=1.1 and the ratio of trisulfide-GH in extract G: reference sample was 2.6%:3.1%=0.8.

This showed that the amount of trisulfide-GH can be reduced by the addition of a metal salt and a low pH.

Example 6

Comparison of Buffers and pH

250 µl of pure hGH (from the production of Genotropin®) in water (2.436 mg/ml)+250 µl of different 100 mM buffers, see Table 1, were mixed. Saturated $H_2S$ (0.11 M) in distilled water was used immediately after preparation. 50 µl of distilled water (control) or H₂S in three different dilutions was added to each sample. (0.5, 0.1 and 0.02 mM H₂S respectively)

The concentration was thereafter 1.11 mg hGH/ml.

These solutions were incubated with the different concentrations of H₂S during 3 hours at room temperature for the preparation of the trisulfide variant of hGH.

After incubation, freezing, thawing and desalting of all samples in 25 mM Tris-HCl at pH 7.6, the amount of trisulfide was analyzed.

The buffers were prepared according to standard tables.

TABLE 1

| |
|---|
| Na-phosphate, pH 7.8 |
| Na-phosphate, pH 7.0 |
| Na-phosphate, pH 6.5 |
| Na-phosphate, pH 6.0 |
| Na-citrate, pH 6.2 |
| Tris-HCl, pH 7.6 |
| Ammonium citrate, pH 6.2 |

Figure 2:
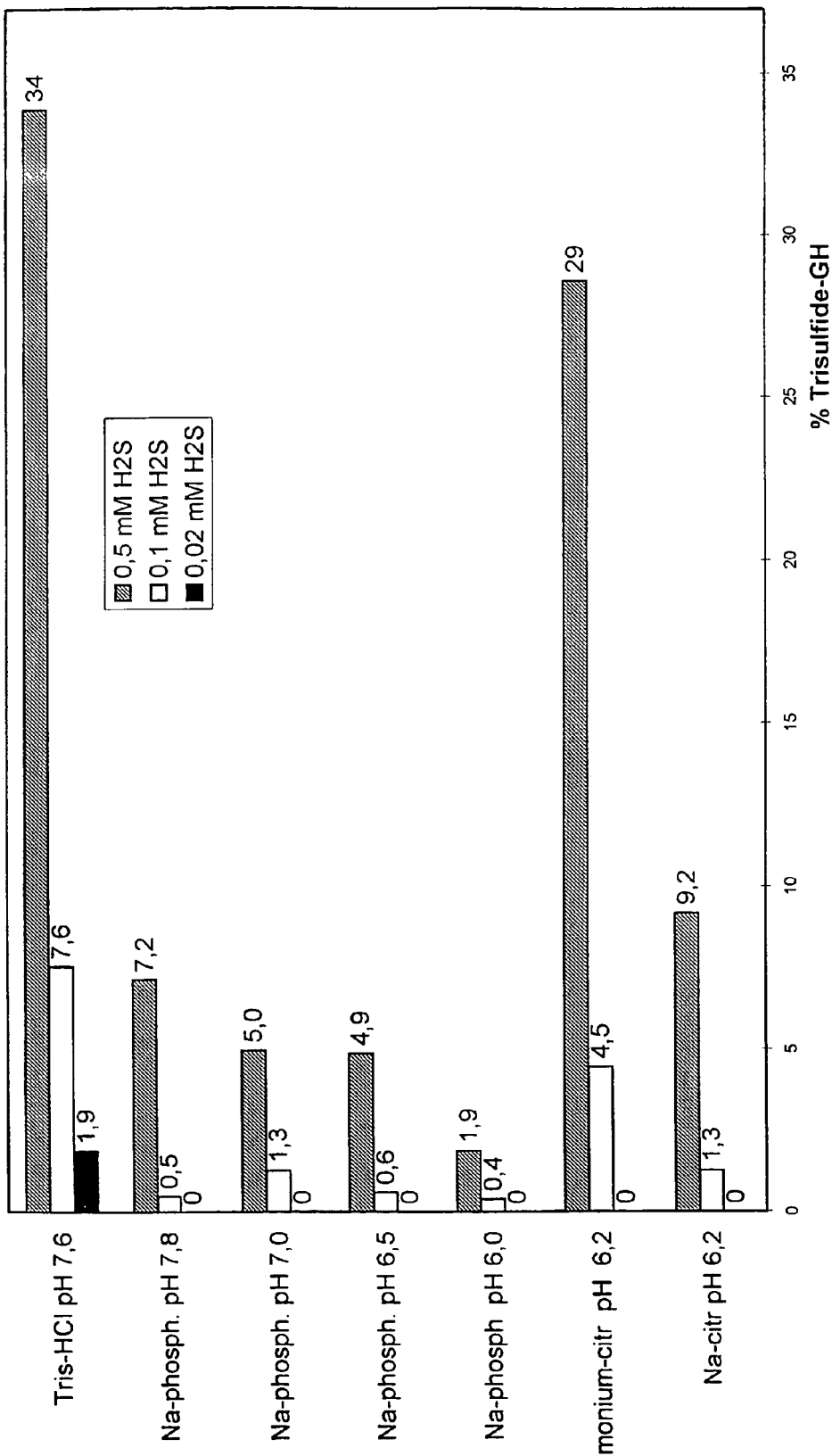
FIG. 2 shows the induction and inhibition of trisulfide formation in GH.

The result is shown in FIG. 2.

Ammonium citrate gave no reduction of trisulfides despite the low pH.

Na-phosphate at pH 6.0 gave the best result but also Na-phosphate at higher pH can be used.

This showed that for pure hGH the addition of a metal salt is of importance for the amount of trisulfides.

The invention claimed is:

1. Method for the production of recombinant growth hormone, comprising fermenting cells to produce recombinant growth hormone, wherein a metal salt is added to a concentrate of the fermented cells after the fermentation step, prior to growth hormone isolation, and wherein the pH of the cell concentrate after the addition of the metal salt is less than or equal to 7, thereby reducing the amount of trisulfides formed in the production of the growth hormone, with the proviso that the production does not include conversion of formed trisulfide growth hormone into native growth hormone form after the addition of the metal salt.

2. Method according to claim 1, wherein the addition is performed directly after fermentation.

3. Method according to claim 1, wherein pH of the cell concentrate after the addition of the metal salt is equal to or lower than pH 6.8.

4. Method according to claim 1, wherein the metal salt is potassium or sodium salt.

5. Method according to claim 4, in which the salt is potassium or sodium phosphate or acetate.

6. Method according to claim 1, wherein the metal salt is an alkali metal salt or an alkali earth metal salt.

7. Method according to claim 1, wherein the peptide is human growth hormone.

8. Method for the production of recombinant peptides, comprising fermenting cells to produce recombinant peptides, wherein a metal salt is added to a concentrate of the fermented cells after the fermentation step, prior to peptide isolation, and wherein the pH of the cell concentrate after the addition of the metal salt is less than or equal to 7, thereby reducing the amount of trisulfides formed in the production of the recombinant peptide, with the proviso that the production does not include conversion of formed trisulfide peptide into native peptide form after the addition of the metal salt.

9. Method according to claim 8, wherein the addition is performed directly after fermentation.

10. Method according to claim 8, wherein the metal salt is an alkali metal salt or an alkali earth metal salt.

11. Method according to claim 8, wherein the metal salt is potassium or sodium salt.

12. Method according to claim 11 in which the salt is potassium or sodium phosphate or acetate.

13. Method according to claim 8, wherein pH of the cell concentrate after the addition of the metal salt is equal to or lower than pH 6.8.

* * * * *